United States Patent
Hoenninger, III

(10) Patent No.: US 9,468,713 B2
(45) Date of Patent: Oct. 18, 2016

(54) APPARATUS AND METHOD OF MITIGATING FREE FLOW IN A FLUID ADMINISTRATION SET

(71) Applicant: John C. Hoenninger, III, Deerfield, IL (US)

(72) Inventor: John C. Hoenninger, III, Deerfield, IL (US)

(73) Assignee: Hospira, Inc., Lake Forest, IL (US)

( * ) Notice: Subject to any disclaimer, the term of this patent is extended or adjusted under 35 U.S.C. 154(b) by 514 days.

(21) Appl. No.: 14/067,083

(22) Filed: Oct. 30, 2013

(65) Prior Publication Data

US 2014/0121601 A1 May 1, 2014

Related U.S. Application Data

(60) Provisional application No. 61/720,095, filed on Oct. 30, 2012.

(51) Int. Cl.
| | | |
|---|---|---|
| A61M 5/00 | (2006.01) | |
| A61M 5/14 | (2006.01) | |
| A61M 5/168 | (2006.01) | |
| A61M 39/28 | (2006.01) | |

(52) U.S. Cl.
CPC ....... *A61M 5/1413* (2013.01); *A61M 5/16881* (2013.01); *A61M 39/28* (2013.01); *A61M 2205/12* (2013.01); *A61M 2205/121* (2013.01); *A61M 2205/6045* (2013.01); *Y10T 29/49716* (2015.01)

(58) Field of Classification Search
CPC ............... A61M 2205/121; A61M 2205/122; A61M 2005/14268; A61M 2209/086; A61M 2209/084; A61M 2205/12; A61M 2205/128; A61M 2205/6045; A61M 2209/082; A61M 5/1413

See application file for complete search history.

(56) References Cited

U.S. PATENT DOCUMENTS

| | | | | |
|---|---|---|---|---|
| 3,771,862 | A * | 11/1973 | Land | G03D 9/00 352/130 |
| 3,985,133 | A * | 10/1976 | Jenkins | A61M 5/172 128/DIG. 12 |
| 4,482,347 | A * | 11/1984 | Borsanyi | A61M 5/14228 128/DIG. 12 |
| 4,842,584 | A * | 6/1989 | Pastrone | A61M 5/14224 604/153 |
| 5,403,277 | A * | 4/1995 | Dodge | A61M 1/0058 604/30 |
| 5,601,420 | A * | 2/1997 | Warner | A61M 5/14228 128/DIG. 12 |
| 5,630,710 | A * | 5/1997 | Tune | A61M 5/172 417/326 |
| 7,077,650 | B2 * | 7/2006 | Johnstone | A61G 15/18 137/355.17 |
| 2011/0015610 | A1 * | 1/2011 | Plahey | A61M 1/28 604/500 |

(Continued)

FOREIGN PATENT DOCUMENTS

| | | |
|---|---|---|
| EP | 0197705 | 10/1986 |
| EP | 0450736 | 10/1991 |
| EP | 0839062 | 9/2004 |

(Continued)

*Primary Examiner* — Kevin C Sirmons
*Assistant Examiner* — William Carpenter
(74) *Attorney, Agent, or Firm* — Michael R. Crabb

(57) ABSTRACT

A free flow mitigating device for a fluid administration set includes a pump driver mechanism having a locator pin attached and positioned to register with a locator hole on the administration set, for example in a cassette. The locator pin has a surface area. A compressible material is attached to at least a portion of the surface area of the locator pin. The compressible material has a thickness such that it is frictionally received within the locator hole of the cassette sufficient to provide a retaining force to resist cassette movement during closing of a flow regulator valve of the cassette.

14 Claims, 9 Drawing Sheets

(56) References Cited

U.S. PATENT DOCUMENTS

2011/0313318 A1* 12/2011 Rule .................... A61B 5/1427
　　　　　　　　　　　　　　　　　　　　　600/581
2011/0313358 A1* 12/2011 Hariharesan ...... A61M 5/14228
　　　　　　　　　　　　　　　　　　　　　604/151

FOREIGN PATENT DOCUMENTS

| | | |
|---|---|---|
| JP | 8509898 | 6/2002 |
| WO | 9813080 | 4/1998 |
| WO | 9910028 | 3/1999 |
| WO | 2011/159956 | 12/2011 |

* cited by examiner

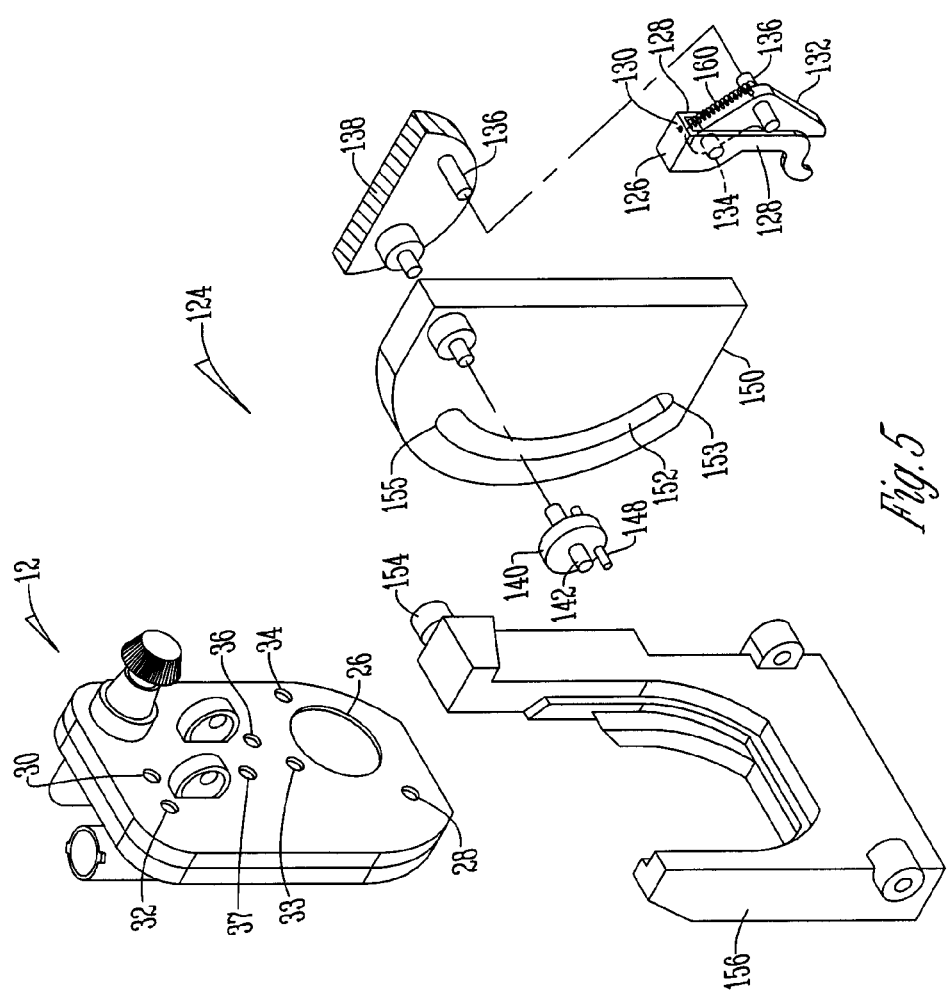

ns set, and
more particularly to a device and method of mitigating free
flow within a fluid administration set.

APPARATUS AND METHOD OF MITIGATING FREE FLOW IN A FLUID ADMINISTRATION SET

BACKGROUND OF THE INVENTION

This invention relates to a fluid administration set, and more particularly to a device and method of mitigating free flow within a fluid administration set.

Fluid administration sets are well-known in the art and included or received in devices such as infusion pumps. Fluid administration sets may include a cassette. With conventional pumping mechanisms, when the infusion pump cassette door, roller, pivot pin or pivot plate are damaged, the administration set cassette can still be loaded successfully by pushing on the cassette door as the door lever is closed. For example, even when the door or door lever is damaged, clinicians may press the cassette door closed. When subsequently opened, there is not always sufficient retentive force on the cassette by the door for the pumping mechanism to work against when it attempts to close the cassette flow regulator valve. This might result in a free flow condition through the administration set, which creates a potential for risk to a patient's health. Therefore, a need exists in the art for a device and method that addresses these issues.

Therefore, an objective of the present invention is to provide a device and method that mitigates the free flow in an administration set.

A further objective of the present invention is to provide a device and method that mitigates free flow in an administration set that is capable of being retrofitted to existing infusers.

A still further objective of the present invention is to provide a device and method that mitigates free flow in an administration set that does not substantially change the manufacturing and assembly process for infusers or administration sets.

These and other objectives will be apparent to those of skill in the art based upon the following written description, drawings and claims.

SUMMARY OF THE INVENTION

A device and method for mitigating free flow in a fluid administration set includes a pumping mechanism having a mechanism plate and a locator pin extending outwardly from the mechanism plate. The locator pin has a surface area thereon. A compressible material is attached to at least a portion of the surface area of the locator pin. The compressible material is of a thickness sufficient to frictionally engage a locator hole in administration set such as a cassette. The compressible material also provides a sufficient retentive force on the administration set that when the door of the pumping mechanism is opened the flow regulator valve is closed.

BRIEF DESCRIPTION OF THE DRAWINGS

FIG. 5 is a perspective view of a cassette and a flow regulator shut off assembly of a driver mechanism;

DETAILED DESCRIPTION OF THE PREFERRED EMBODIMENTS

Figure 4:
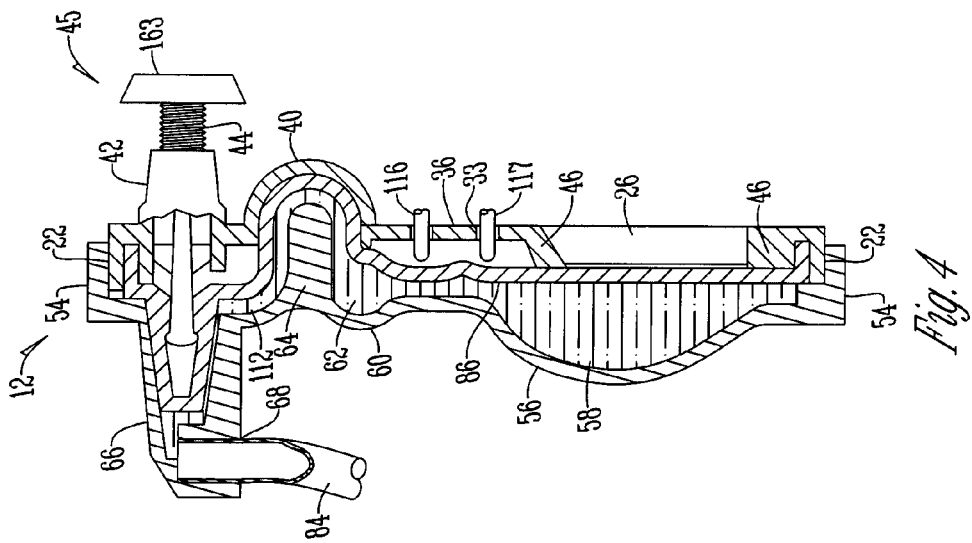
FIG. 4 is a cross sectional view taken along the plane of line 4-4 of FIG. 2
Figure 3:
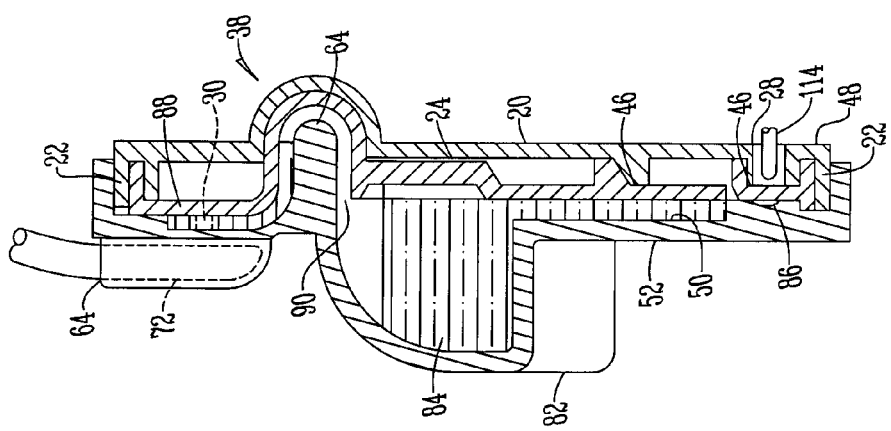
FIG. 3 is a cross sectional view taken along the plane of line 3-3 of FIG. 2.

Referring to the Figures, a device 10 for the administration of fluid to a patient includes a fluid administration set or device 12 such as a cassette or the like. In one example, device 12 has a rigid face member 14, a rigid back member 16, and an elastomeric member 18 positioned between. Face member 14 has a generally flat exterior face 20 with an inwardly extending peripheral flange 22 and interior face 24. Extending through face member 14 is plunger opening 26, pumping chamber inlet valve actuator opening 28, primary inlet valve actuator opening 30, secondary inlet valve actuator opening 32, pumping chamber outlet valve actuator opening 33, locator pin opening 34 in face member 14, proximal pressure sensor opening 37 and distal pressure sensor opening 36. Extending outwardly from face member 14 are proximal air-in-line sensor 38 and distal air-in-line sensor 40 and cylindrical housing 42. Housing 42 receives the plunger 44 of flow regulator 45 and is configured to allow plunger 44 to be threaded inwardly of housing 42 to reduce or prevent the flow of fluid through regulator 45, or to be threaded outwardly of cylindrical housing 42 to increase or allow fluid to flow through regulator 45 when the administration set is used for gravity flow infusion without an infusion pump. Flow regulator 45 may alternately be axially pushed closed to prevent fluid flow or axially pulled open to allow free flow or flow control by an infusion pump mechanism. Interior face 24 has flanges 46 and 48, as best seen in FIGS. 3 and 4.

Figure 2:
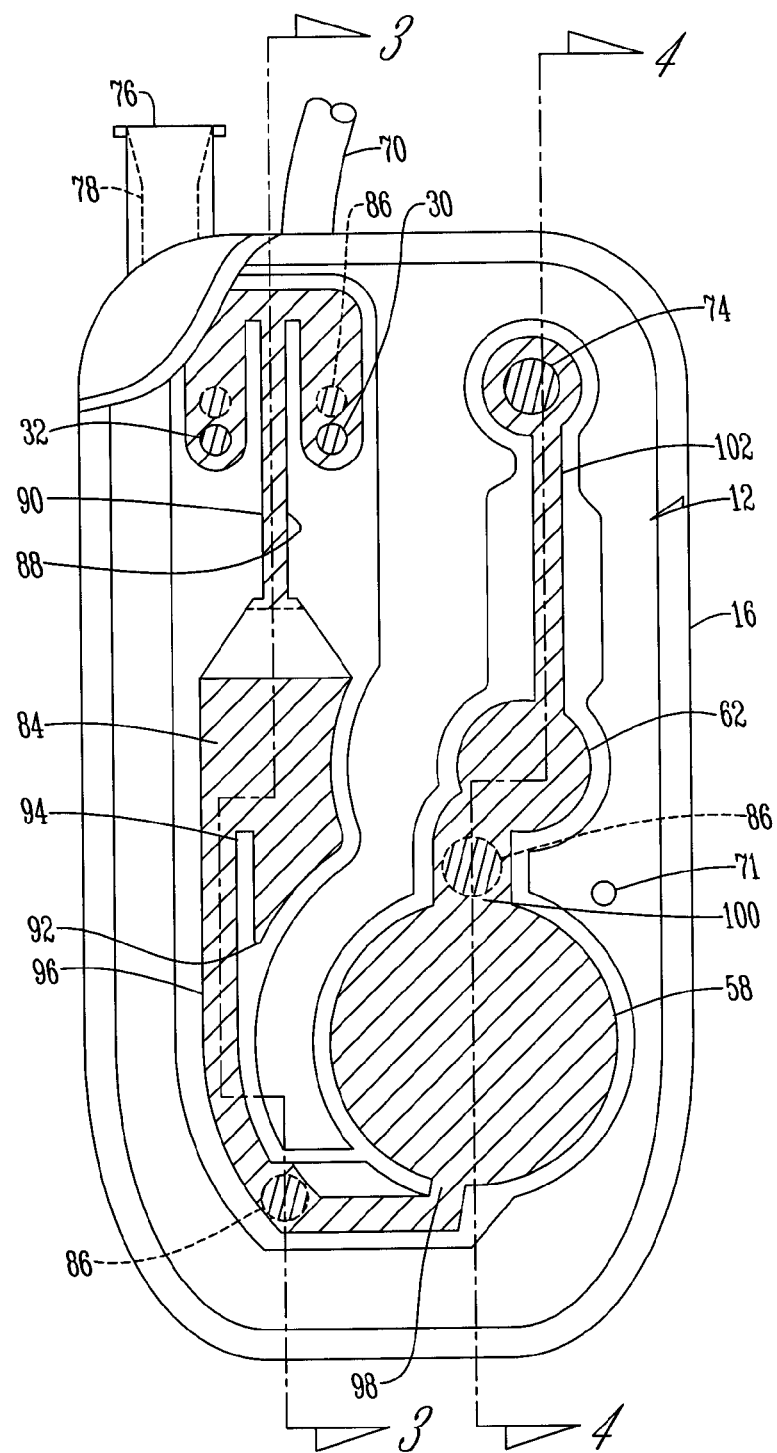
FIG. 2 is a plan view of the cassette with one face broken away.

Back member 16 has an inside surface 50, an outside surface 52 and peripheral flange 54 that which nests with peripheral flange 22 of face member 14. Flanges 54 and 22 are secured together in a sealed fashion by welding, gluing and the like. In general alignment and behind the plunger opening 26 is an enlarged recess 56 that forms a pumping chamber 58. Behind distal pressure sensor opening 36 of face member 14 is recess 60 that forms distal pressure chamber 62. Extending partially into the proximal air-in-line sensor 38 and the distal air-in-line sensor 40 of face member 14 respectively is a corresponding finger 64. Behind the cylindrical housing 42 of the face member 14 is a plunger recess 66 that receives the plunger 44 of the flow regulator 45. Plunger recess 66 also has an outlet 68 with a distal tube 84 extending from the outlet 68 to a patient's arm. Aligned with locator pin opening 34 on face member 14 is a second locator pin opening 71 on back member 16, as best seen in FIG. 2.

To the side of plunger recess 66 is a primary inlet 70 which has an inlet passage 72 having a primary inlet valve opening 30. Adjacent primary inlet 70 is a secondary inlet 76 which has a second inlet passage 78 having a secondary inlet valve opening 32. Below primary and secondary inlets 70 and 76 is a reservoir recess 82 which forms proximal air reservoir 84. Behind primary valve opening 30, secondary inlet valve opening 32, and pumping chamber inlet valve actuator opening 28 are valve seats 86. Extending from openings 30 and 32 to reservoir 84 is channel 88. Reservoir 84 has a reservoir inlet 90, a reservoir bottom 92 and a reservoir outlet 94. Reservoir outlet 94 is in fluid communication with channel 96, which is fluid communication with pumping chamber 58 through pump chamber inlet 98. A short channel 100 fluidly connects pumping chamber 58 with distal pressure chamber 62 and channel 102 fluidly connects the distal pressure chamber 62 through distal air-in-line sensor 40 to cassette fluid outlet 68.

The elastomeric member 18 extends between face member 14 and back member 16 to cover openings on face member 14 and reservoirs and channels on the back member 16. The elastomeric member is received within flanges 22, 46 and 48 on the face member 14.

Figure 1:
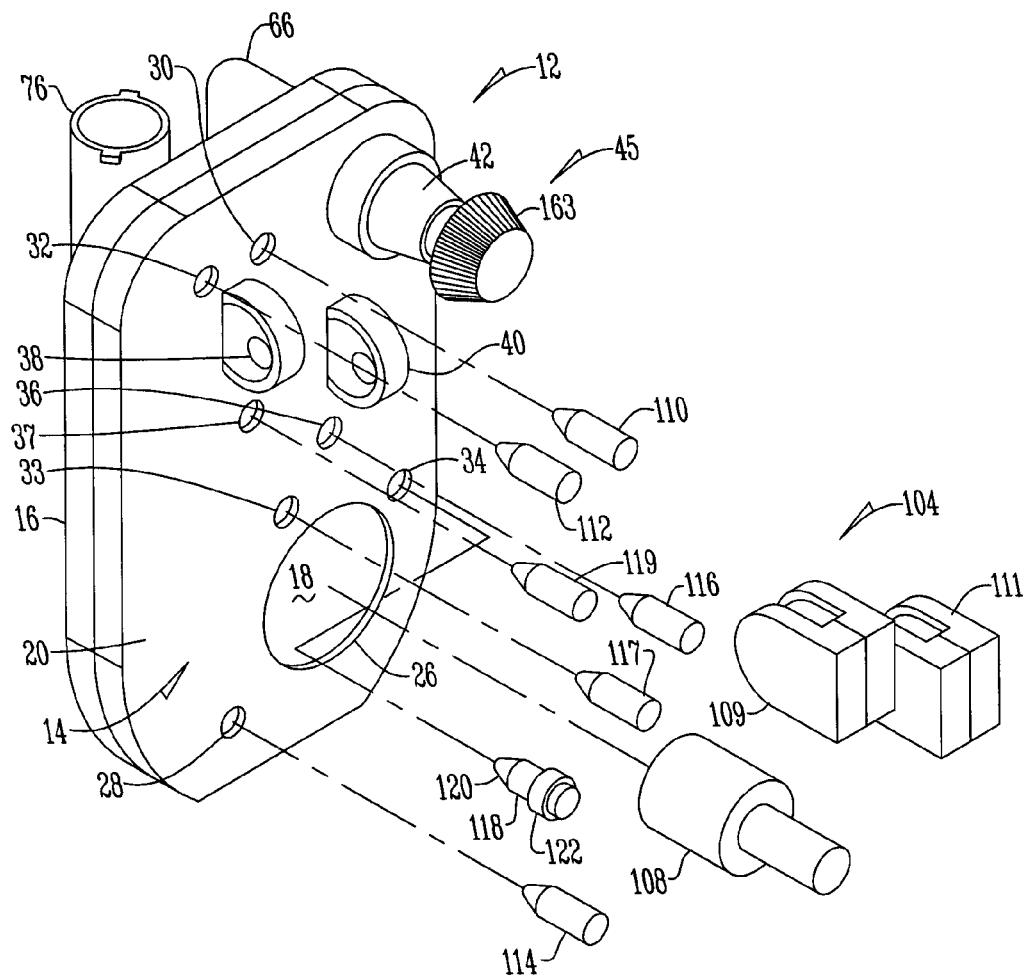
FIG. 1 is a perspective view of a portion of an administration set such as cassette along with selected portions of a driver mechanism.
Figure 10:
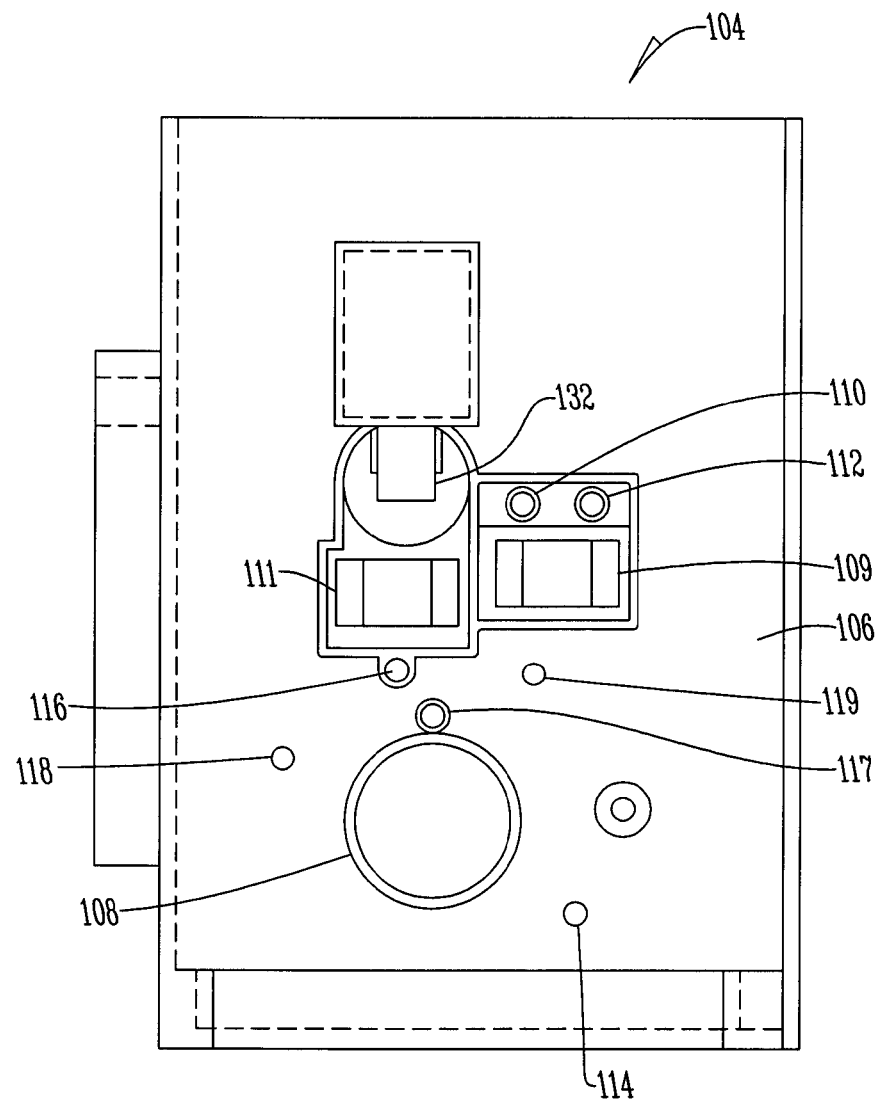
FIG. 10 is a front view of a portion of a driver mechanism.
Figure 11:
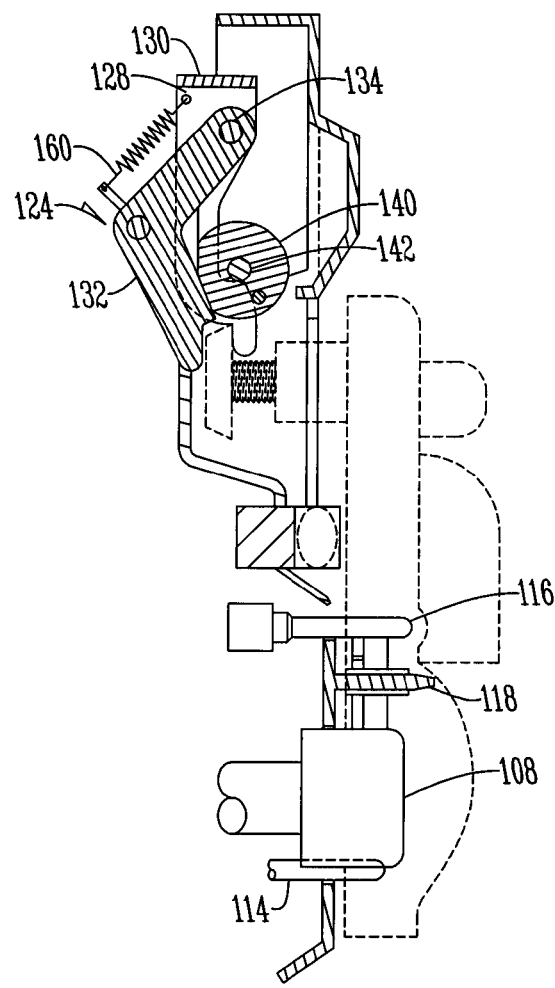
FIG. 11 is a sectional view of a cassette and a flow regulator shut off assembly.
Figure 12:
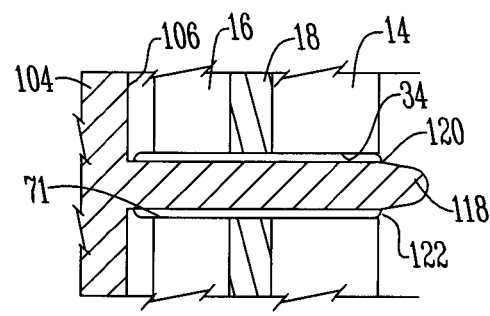
FIG. 12 is a side sectional view of a first embodiment of a cassette locator pin with a retentive gasket made of a compressible material.

As best seen in FIGS. 1 and 10, a pumping or pump driver mechanism 104 has a front mechanism plate 106. Extending outwardly from the mechanism plate 106 is a movable plunger 108 that is aligned with and received by plunger opening 26. Also extending outwardly from the mechanism plate 106 are primary and secondary inlet actuators 110 and 112 that are aligned with and received by primary inlet valve opening 30 and secondary inlet valve opening 32 respectively. Aligned with and received by proximal pressure sensor opening 37 is a pressure sensor pin 119 that extends outwardly from mechanism plate 106. Aligned with and received by inlet valve actuator opening 28 is actuator 114 which extends outwardly from mechanism plate 106. Aligned with and received by distal pressure sensor opening 36 is a pressure sensor pin 116 that extends outwardly from mechanism plate 106. Aligned with proximal air-in-line sensor opening 38 is an air-in-line sensor 109 that extends outwardly from mechanism plate 106. Aligned with distal air-in-line sensor opening 40 is an air-in-line sensor 111 that extends outwardly from mechanism plate 106. Aligned with and received by outlet valve actuator opening 33 is a pumping chamber outlet valve actuator 117. Finally, extending outwardly from the mechanism plate 106 and aligned with and received by locator pin opening 71 and/or second locator pin opening 34 is a locator pin 118 having a surface area 120 as shown in FIG. 12. The locator pin 118 can be integrally formed with or separately formed and attached to the plate 106. Attached to at least a portion of the surface area 120 of the locator pin 118 is a compressible material 122. The compressible material 122 frictionally engages cassette locator pin openings 71 and/or 34 and thus inhibits slippage or unintended movement of the cassette axially along the locator pin 118.

Figure 13:
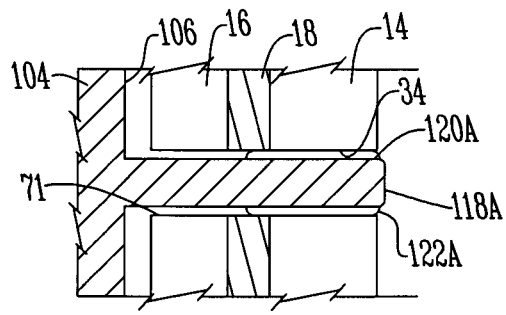
FIG. 13 is a side sectional view of the second embodiment of a cassette locator pin with a retentive gasket made of a compressible material.
Figure 14:
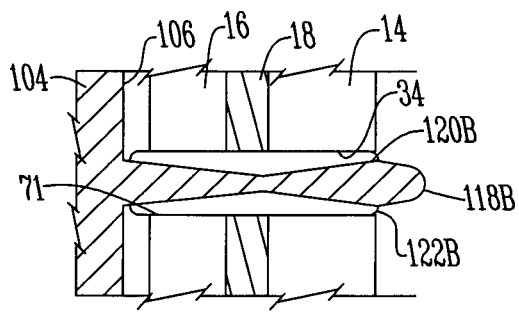
FIG. 14 is a side sectional view of the third embodiment of a cassette locator pin with a retentive gasket made of a compressible material.
Figure 15:
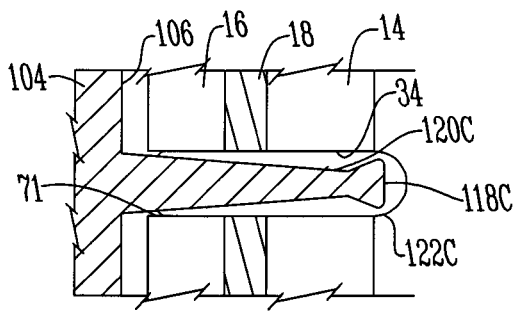
FIG. 15 is a side sectional view of the fourth embodiment of a cassette locator pin with a retentive gasket made of a compressible material.

The locator pin 118 is of any shape and/or size. Shapes and sizes that correspond or mate with the openings 71 and/or 34 work well. For example the locator pin 118 is generally cylindrical and preferably is of a length sufficient to fit into or, more preferably, through actuator pin openings 71 and/or 34 of cassette 12. As an example, the locator pin can have a flat end opposite the end attached to the mechanism plate 106 as shown with embodiments 118A and 118C in FIGS. 13 and 15 respectively. Alternatively, the locator pin can be tapered at one or both ends as shown with embodiments 118, 118B, and 118C in FIGS. 12, 14, and 15 respectively. As seen in FIG. 12, the locator pin 118 can have a relatively short lead-in taper at its unattached end that defines a blunt conical tip. The blunt conical tip aids in centering and guiding the locator pin into the openings. In FIG. 14, the locator pin 118B has a similar blunt conical tip, but also has a necked in intermediate portion that has a diameter that is smaller than the diameters adjacent either end of the pin. This necked in intermediate portion can assist in attachment of the compressible material 122B to the pin 118B and provide tighter frictional gripping forces between the material and the walls of the openings. In FIG. 15, the locator pin 118C also has a necked in portion, but it is juxtaposition adjacent to the free end of the pin or opposite of the attached end. The compressible material can extend over the full length of the locator pin, as shown by 122C in FIG. 15, or just cover a portion such that it engages one or more of the openings 71 and/or 34, as shown by 122, 122A and 122B in FIGS. 12-14. The compressible material can also cover only a small portion of the locator pin such that it only engages the elastomeric member 18 of the cassette of the administration set. The opposite ends of the compressible material can be rounded or angled to reduce wear and breakdown of the corners and facilitate repetitive engagement with the openings of the cassette.

As best seen in FIGS. 5-9 and 11, the pump mechanism 104 also has a flow regulator shut off assembly 124. The flow regulator shut off assembly 124 pulls plunger 44 rapidly outward into the open position when the cassette 12 is mounted in the pump driver mechanism 104, and pushes the plunger 44 inward into the "off" or closed position when the user is ready to remove the cassette from the driver mechanism 104. Flow regulator shut off assembly 124 includes a gripper bracket 126 having two downwardly depending arms 128 joined by a connecting portion 130 at their upper ends. Pivotally mounted between arms 128 is a chevron-shaped depressor member 132. Depressor member 132 is pivotally mounted to and between arms 128 by a pin 134. Depressor member 132 is also pivotally mounted about a pin 136 which is fixedly mounted on a chassis 138 (not shown). Also mounted between arms 128 is a cam 140 which is fixedly mounted on a rotatable shaft 142. Cam 140 has cam surfaces 144 which engage corresponding cam surfaces 146 on the inside of depressor member 132. Cam 140 further includes a driving pin 148, which extends through cam 140 to engage the lower ends of arms 128.

Flow regulator shut off assembly 124 further includes a slotted pivot arm 150 which is fixedly secured to rotatable shaft 142 to rotate freely about its longitudinal axis but to restrain it from translational movement in horizontal or vertical directions. Pivot arm 150 will therefore pivot in tandem with cam 140. Pivot arm 150 has a slot 152 in which a roller 154 is free to slide. Roller 154 is mounted on the driver door 156 in which cassette 12 is mounted when in the driver 104. The driver door 156 is pivotally mounted on a pin 158, which is also fixedly secured to chassis 138 (not shown) of driver 104.

Figure 6:
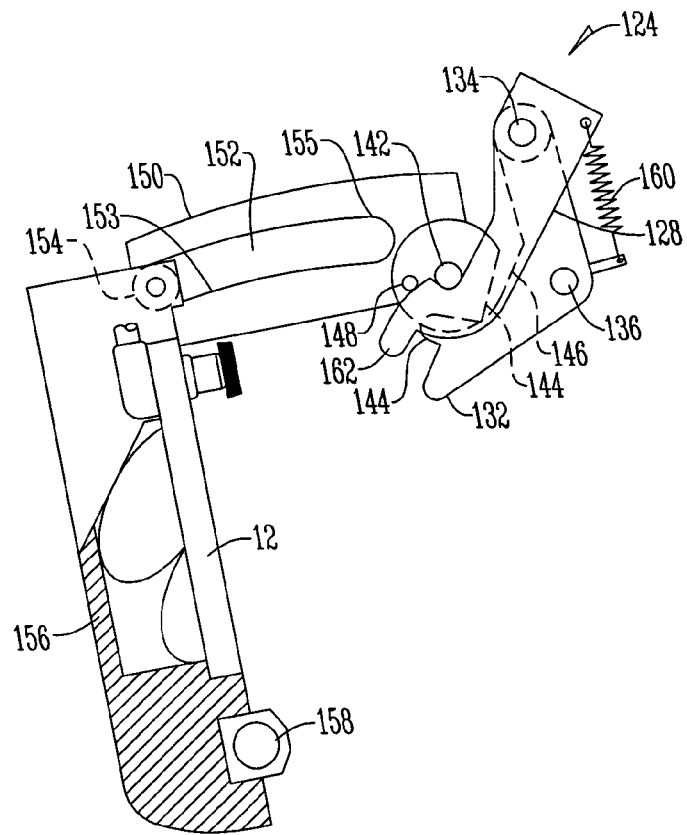
FIG. 6 is a detailed view partially in section of a cassette mounted in a door of a driver having a flow regulator shut off assembly.

As can be seen in FIG. 6, when driver door 156 is open, pivot arm 150 is in a substantially horizontal position with roller 154 at the distal or far end 153 of slot 152. When door 156 is pivoted to the vertical, closed position shown in FIG. 5, roller 154 travels in slot 152 and forces pivot arm 150 to rotate in a counterclockwise direction from the position shown in FIG. 6 to the position shown in FIG. 5 where roller 154 is in the proximal or near end 155 of slot 152. As pivot arm 150 pivots from the substantially horizontal position shown in FIG. 6 to the substantially vertical position shown in FIG. 5, it rotates shaft 142 since pivot arm 150 is fixedly attached to shaft 142. As shaft 142 rotates in a counterclockwise direction, it forces cam 140 to do likewise. As cam 140 rotates counterclockwise (FIG. 7), the ends of driving pin 148 engage the lower ends of arms 128, forcing gripper bracket 126 to pivot about pin 134. In addition, the counterclockwise rotation of cam 140 forces depressor member 132 to pivot about pin 136. The counterclockwise rotation of cam 140 forces cam surface 144 against cam surface 146 to urge depressor member 132 to rotate in a clockwise direction about pin 136 until cam surface 144 engages cam surface 146 as shown in FIG. 7.

Figure 8:
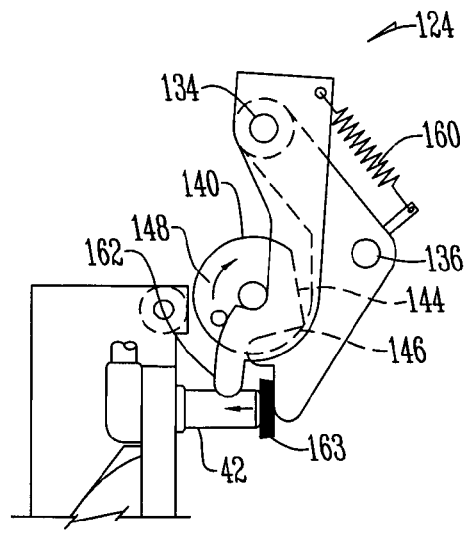
Figure 9:
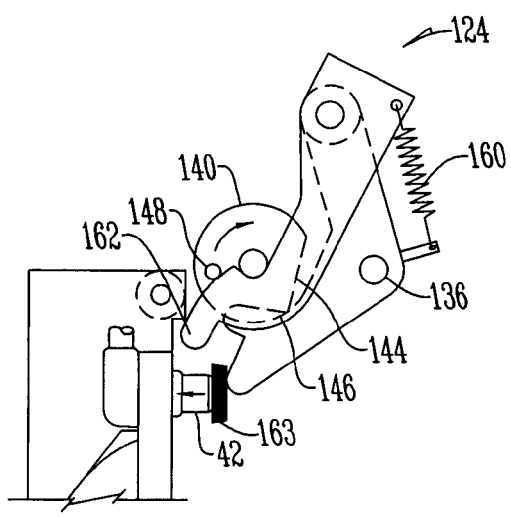

When door 156 is opened again (i.e. pivoted toward the position shown in FIG. 6) pivot arm 150 pivots from the substantially vertical position shown in FIG. 5 toward the substantially horizontal position shown in FIG. 6, forcing cam 140 to rotate clockwise (FIG. 8). As cam 140 rotates clockwise, driving pin 148 releases the lower ends of arms 128 and a spring 160 between gripper bracket 126 and depressor member 132 urges gripper bracket 126 to pivot clockwise about pin 134 to return to the position of FIG. 6.

Figure 7:
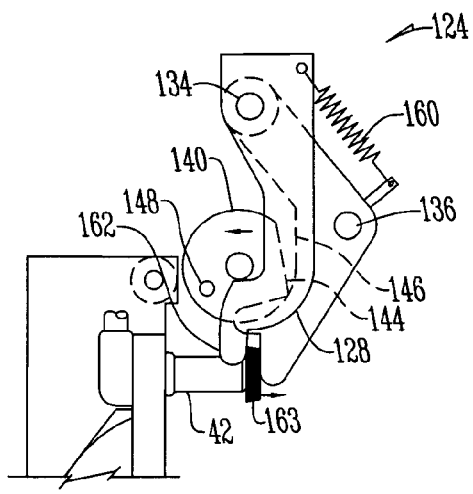
FIGS. 7-9 are detailed views of a flow regulator shut off assembly of a driver mechanism.

As cam 140 rotates clockwise as shown in FIG. 8, cam surface 144 engages cam surface 146 to force depressor member 132 to pivot in a clockwise direction about pin 136 to return to position of FIG. 6 from position of FIG. 7, the position of FIG. 8 being an intermediate position between the positions of FIGS. 7 and 6.

The lower ends of arm 128 include gripper fingers 162. When cassette 12 is mounted in the door and the door is pivoted toward the closed position, the knob 163 (FIGS. 6-9) of plunger 44 passes beneath the ends of fingers 162 to a position adjacent to the lower end of depressor member 132. As cam 140 drives gripper bracket 126 and depressor member 132 toward the closed position of FIG. 7, the fingers 162 trap knob 163 between fingers 162 and the lower end of depressor member 132 and pull plunger 44 outwardly of cylindrical housing 42 to open the flow regulator 45 completely.

Conversely, when door 146 is pivoted from the closed position toward the opened position, roller 154 forces pivot arm 150 to rotate cam 140 in a counterclockwise direction which allows fingers 162 to move away from the lower end of depressor member 132 to release knob 163 from flow regulator shut off assembly 124. As knob 163 is being released, cam 140 pivots depressor member 132 such that the lower end of depressor member 132 depresses or urges plunger 44 inwardly of housing 42 (See FIGS. 8 and 9) so that flow regulator 45 is closed and prevents fluid from flowing through the cassette. When the door is fully opened (FIG. 6), the flow regulator is off and the cassette can be removed. It is important that flow regulator be turned off before the cassette is no longer in contact with the outlet valve actuator 117. Otherwise, fluid would flow through the cassette in an uncontrolled fashion under the force of gravity. Other details of the structure and operation of the flow regulator shut off assembly are shown and described in U.S. Pat. No. 4,842,584, which is incorporated in its entirety by reference herein.

As can be seen, when cassette 12 is mounted in the driver door 156 and driver door 156 is closed, flow regulator 45 is opened completely by shut off assembly 124. However, as door 156 is opened to remove cassette 12 from the driver, shut off assembly 124 closes flow regulator 45 to prevent fluid from flowing through the cassette at an uncontrolled rate. Unfortunately the external force required to close the flow regulator valve 45 is applied in a direction and location such that it tends to create a tipping moment on the cassette 12 and pull it away from the mechanism plate 106 axially along the locator pin 118. Thus the cassette 12 may prematurely lose contact with the outlet valve actuator 117 of the pump driver mechanism 104, which might allow unintended free flow from the administration set.

In the event that the door 156, door pivot 158 or roller 154 becomes damaged and does not have sufficient retentive action on the cassette 12, the additional retentive force or action of the compressible material 122 on locator pin 118 provides a mitigating retentive action to ensure that the flow regulator valve 45 closes. The compressible material 122 is of a thickness that presses outwardly on and frictionally engages the sidewall of at least one of the cassette locator holes 34 and 71 when the door 156 is closed without impeding door 156 from closing or opening. When the door 156 is opened, the compressible material 122 acts in parallel with the door 156 to provide a retentive force that the mechanism can work against to close the flow regulator valve 45. In the case where the door 156 is damaged and provides insufficient retentive force, the compressible material 122 provides sufficient retentive force to allow the flow regulator shut off assembly 124 to successfully close the flow regulator valve 45. This prevents a free flow condition in the administration set. The compressible material is either installed during the manufacture of the locator pin 118 or is retrofitted to an existing device.

To retrofit an existing driver 104 a cassette locator pin 118 having sufficient length to extend through locator pin openings 71 and/or 34 is attached to the mechanism plate 106 of driver 104 in any conventional manner. Before or after the pin 118 is attached, the compressible material 122 can be attached to the surface area 120 of the locator pin. An existing locator pin can be detached from the mechanism plate 106 and replaced with a new locator pin 118 having compressible material made and pre-attached as discussed herein.

The compressible material 122 forming the retentive gasket can be made and installed on the locator pin in a number of ways from a number of different gasket materials, including but not limited to the following:

1) Tubing, for example tubing that is designed to shrink under heating to a specified shape:
   a) Elastomeric tubes that maintain high flexibility even at low temperatures, are resistant to many chemicals and have good resistance to abrasion. A common shrink ratio is 2:1.
   b) Silicone rubber that offers excellent resistance to scrape abrasion and high flexibility.
   c) Polyolefin tubes that have maximum continuous use temperatures from −55 to 135° C. A common shrink ratio is 2:1.
   d) PVC tubes that are abrasion-resistant, as well as tolerant of cleaning chemicals and UV radiation used for sterilization in medical applications.

2) Molded and extruded gaskets of a specified shape and properties that can be made with the following materials, and in some cases overmolded onto the locator pin:
   a) Neoprene, which has high tensile strength, excellent heat and chemical resistance, and compression set, tear and abrasion resistance.
   b) Silicone, for example Dow Corning XIAMETER™ brand silicone high consistency rubber (HCR), which can be injection molded to meet dimensional tolerances.

c) Fluoro-elastomer (DuPont Viton™) moldable elastomer polymer that has excellent heat and chemical resistance, and compression set, tear and abrasion resistance.
d) Urethane (Polyethylene-apdate, Poly (oxy-1, 4, butylene ether based), which has excellent abrasion, tear, and solvent resistance.
e) Buna-N (Nitrile) elastomer rubber with excellent resistance to petroleum products, as well as compression set, tear and abrasion resistance.
f) Thermoplastic Elastomer (TPE) elastomer plastic that is slip resistant, shock absorbing and flexible.

Based upon the foregoing it can be seen that the present invention at least accomplishes its stated objectives. It should be understood, of course, that the foregoing relates to exemplary embodiments of the disclosure and that modifications may be made without departing from the scope of the following claims.

What is claimed is:

1. A device for mitigating free flow in an infusion pump that receives a fluid administration set, comprising:
   a pump driver mechanism having a locator pin that extends outwardly from a mechanism plate;
   an administration set having a locator hole that registers with the locator pin;
   wherein the locator pin has a surface area; and
   a compressible material positioned on at least a portion of the surface area of the locator pin and retaining the administration set by frictional engagement with the locator hole.

2. The device of claim 1 wherein the compressible material is frictionally received within the locator hole when the administration set is placed on the locator pin.

3. The device of claim 2 wherein the compressible material has a thickness that provides a sufficient frictional force against a sidewall of the locator hole to oppose a force applied to close a flow regulator valve of a cassette of the administration set.

4. The device of claim 1 wherein the locator pin has opposite ends and a necked-in intermediate portion between the opposite ends.

5. The device of claim 1 wherein the locator pin has opposite ends that include a first end attached to the mechanism plate and a free end opposite the first end, and wherein a necked-in portion is juxtapositioned adjacent to the free end.

6. The device of claim 1 wherein the locator pin has a cylindrical portion and a conical tip.

7. The device of claim 1 wherein the locator pin is tapered at least at one end.

8. The device of claim 1 wherein the compressible material covers the surface area of a free end of the locator pin.

9. The device of claim 1 wherein the locator pin has all exposed portions of the surface area covered completely with the compressible material.

10. The device of claim 1 wherein the mechanism plate is generally upright and the locator pin extends horizontally outwardly from the mechanism plate.

11. A method of retrofitting an infusion pump that receives a fluid administration set with a free flow mitigating device, comprising the steps of:
    attaching a locator pin having a surface area to a mechanism plate of a pump driver mechanism such that the locator pin extends outwardly from the mechanism plate;
    attaching a compressible material to at least a portion of the surface area of the locator pin; and
    providing the administration set having a locator pin opening that registers with the locator pin so as to be retained by frictional engagement with the locator pin opening.

12. The method of claim 11 wherein the administration set includes a cassette and the locator pin has a length sufficient to extend through and out of the locator pin opening on the cassette.

13. The method of claim 12 wherein the compressible material is of a thickness that frictionally engages a sidewall of the locator pin opening of the cassette to provide sufficient retentive force to maintain the cassette fixed in position on the locator pin during movement of a flow regulator valve by an external force.

14. The method of claim 12 wherein the locator pin is tapered at least at one end.

* * * * *